United States Patent [19]

Giem et al.

[11] Patent Number: 4,476,880
[45] Date of Patent: Oct. 16, 1984

[54] APPARATUS FOR SENSING AND INDICATING VAGINAL MUSCLE CONTRACTION

[76] Inventors: David A. Giem, 2315 Francisco Dr., Newport Beach, Calif. 92660; Barry L. Aaronson, 521 Acacia Ave., Corona Del Mar, Calif. 92625; Charles K. Jones, 3607 Valle Vista, Chino, Calif. 91710

[21] Appl. No.: 446,475

[22] Filed: Dec. 3, 1982

[51] Int. Cl.$^3$ .................... A61B 5/00; A61B 17/42
[52] U.S. Cl. ..................................... 128/778; 73/705
[58] Field of Search .................. 128/774, 778; 73/705

[56] References Cited

U.S. PATENT DOCUMENTS

| | | | |
|---|---|---|---|
| 2,507,858 | 5/1950 | Kegel | 128/2 |
| 2,541,520 | 2/1951 | Kegel | 128/2 |
| 2,839,050 | 6/1958 | Sokol | 128/2 |
| 3,119,270 | 2/1961 | Wayne | 73/410 |
| 3,249,760 | 5/1966 | Miller | 250/231 |
| 3,598,106 | 8/1971 | Buning | 128/778 |
| 3,640,284 | 2/1972 | De Langis | 128/2 |
| 3,683,893 | 8/1972 | Fried | 128/2 |
| 4,050,449 | 9/1977 | Castellana et al. | 128/2 |
| 4,167,938 | 9/1979 | Remih | 128/778 |
| 4,289,963 | 9/1981 | Everett | 73/705 X |

FOREIGN PATENT DOCUMENTS

| | | | |
|---|---|---|---|
| 718633 | 9/1965 | Canada | 73/705 |
| 2035453 | 1/1972 | Fed. Rep. of Germany | 128/778 |
| 12527 | 2/1981 | Japan | 73/705 |

*Primary Examiner*—Kyle L. Howell
*Assistant Examiner*—John E. Hanley
*Attorney, Agent, or Firm*—Gausewitz, Carr, Rothenberg & Edwards

[57] ABSTRACT

Vaginal muscle contraction is sensed by change of pressure within a flexible, hollow tubular member that is adapted to be compressed in response to muscle contraction. A simple pressure transducer embodies a pressure tube connected with the tubular sensing member and having an end covered by a flexible diaphragm that expands in response to increased pressure so as to progressively block light transmitted to a photosensitive resistor. The resistor controls an electrical signal that is employed to provide an audible or visual display that provides a measure of relative strength of muscular contraction and which also may be used in a biofeedback loop to inform the user of the intensity of the contraction. Accuracy of the inexpensive transducer is increased by compensating the output electrical signal for both nonlinearity and hysteresis of the distensible rubber diaphragm.

5 Claims, 3 Drawing Figures

APPARATUS FOR SENSING AND INDICATING VAGINAL MUSCLE CONTRACTION

BACKGROUND OF THE INVENTION

The present invention relates to apparatus for measuring and indicating strength of vaginal muscle contractions and more particularly concerns such apparatus uniquely arranged for use with a simplified and inexpensive pressure transducer.

The need for both direct measurement of strength of vaginal muscle contraction and the benefits of providing an indication of such contraction, as is required for exercise of the muscles, have been recognized for many years. A number of devices have been developed for clinical measurement of vaginal muscle strength and for the provision of feedback that displays both occurrence and strength of muscular contractions which may not be otherwise detectable. Apparatus of this type are shown in U.S. Pat. Nos. 2,507,858; 2,541,520; 2,839,050; 3,598,106; 3,640,284; 3,683,893; 4,050,440; and 4,167,938. Devices shown in these patents generally embody pressure sensing mechanisms that provide dials or gauges, or the like, for displaying pressure variations. Instruments of the prior art are fairly bulky, complex, difficult to manufacture, and costly. Accordingly, relatively expensive prior apparatus may be acceptable for clinical use, but is unacceptably complex and costly for use as an individual home exercising apparatus.

SUMMARY OF THE INVENTION

In carrying out principles of the present invention in accordance with a preferred embodiment thereof, a flexible, hollow tubular member adapted to be compressed in response to vaginal muscle contraction is coupled with a simple, inexpensive transducer that provides an electrical signal to an indicator which displays relative intensity of muscle contraction. The transducer is formed of a partitioned housing having a light source in one chamber and a photosensitive resistor in the other chamber. Means responsive to pressure in the tubular member controls the amount of light received by the photosensitive resistor from the light source. Resistance of the photosensitive resistor generates an electrical signal that controls the display. According to a feature of the invention, light is transmitted from one part of the housing to another through an aperture in the partition and a pressure tube in the housing, connected to receive pressure from the tubular sensing member, has its end closed by a flexible diaphragm which flexes to progressively block light transmitted to the photosensitive resistor as pressure in the tube increases. According to still another feature of the invention, the diaphragm is subject to nonlinearity and hysteresis in its flexure, and means are provided to electrically compensate for both nonlinearity and hysteresis so as to improve accuracy and repeatability of an exceedingly simple and inexpensive transducer.

DETAILED DESCRIPTION OF THE INVENTION

Figure 1:
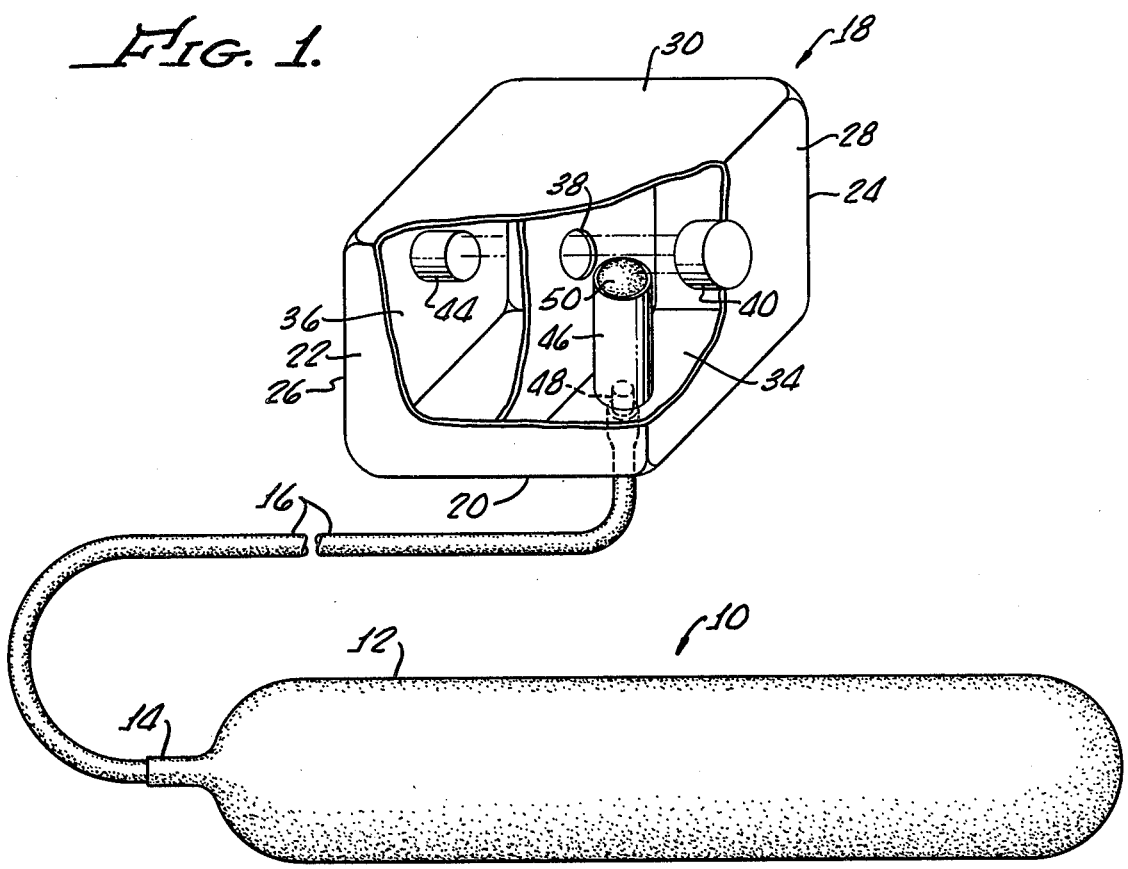
FIG. 1 illustrates a tubular sensing member and transducer embodying principles of the present invention.

As shown in FIG. 1, a hollow, closed tubular member 10 has a thin, but self-supporting flexible wall 12 made of a rubber, such as latex, and formed for insertion into contact with vaginal muscles. Tubular member 10 is connected by means of a fitting 14 and an inextensible tube 16 to a transducer, generally indicated at 18, which transduces pressure within the tubular member 12 into an electrical signal.

Transducer 18 is formed of a light tight housing which, in the illustrated embodiment, is of a generally rectangular configuration having a bottom 20, sidewalls 22 and 24, end walls 26, 28 and a top 30. A partition 32 extends completely across the interior of the housing, dividing it into a light transmitting chamber 34 adjacent end wall 28 and a receiving chamber 36 adjacent end wall 26. An aperture 38 is formed in a central portion of the partition 32 for transmitting light projected from a light source, such as a light emitting diode 40, mounted within chamber 34 upon end wall 28. Mounted upon end wall 26 within the receiving chamber 36 is a photosensitive resistor or photocell 44 which provides an electrical signal of a magnitude related to the amount of light falling upon the resistor. The photocell 44 is positioned to receive light transmitted through aperture 38 from light emitting diode 40.

Fixedly secured to the transducer housing and positioned within light source chamber 34, closely adjacent partition 32, is a rigid pressure tube 46 having a lower end connected by a fitting 48 that extends through the bottom wall of the housing to one end of the connecting tube 16. The upper end of pressure tube 46 is open and sealed with a thin, flexible diaphragm 50 that is fixedly mounted on the tube end. This sealed end of the pressure tube is positioned immediately adjacent the aperture 38 so that when the diaphragm 50 flexes in response to increased pressure within pressure tube 46, light transmitted through the aperture 38 from light emitting diode 40 to the photocell 44 is at least partially blocked. Diaphragm 50 may be formed of a thin rubber, which has a significant amount of stretch and flexibility. Other materials, such as very thin metal or the like, may also be used.

Conveniently, the housing, except for its top, and including the partition, is molded as an integral unit of a suitable rigid plastic. The light source and photocell and pressure tube are then fixedly mounted within the housing, as indicated, with the diaphragm 50 secured to and sealed upon the end of the pressure tube. Top 30 is then secured to the housing sides and ends to provide the pair of light sealed chambers 34, 36.

The housing of transducer 18 is relatively small and, for example, may be approximately two inches long by one and a half inches high by a half inch wide. Pressure tube 46 is also preferably small, having a length of approximately three quarters of an inch and an outside diameter of three eighths of an inch in a presently preferred embodiment. Diaphragm 50 is positioned snugly over the open end and may be made of rubber having a thickness of approximately ten mils. The pressure tube and rubber diaphragm are configured so as to decrease the amount of stretch of the rubber with increase of pressure, thereby to decrease nonlinearity of the output electrical signal caused by nonlinearity in the stretching of the rubber. A larger diameter of the pressure tube will yield less flexing of the diaphragm for a given change in pressure. Aperture 38 may also be suitably shaped so as to decrease effects of nonlinearity of the rubber flexing or stretching. This entails shaping the aperture so as to conform to the profiles of the diaphragm 50 as the diaphragm expands with increase in pressure. For example, the shape of the profiles of the diaphragm (on a plane perpendicular to the axis of light transmitted from the diode 40) may be plotted and aperture 38 shaped so that the area of the aperture blocked by the flexed diaphragm will have a more linear relation to the magnitude of pressure within pressure tube 46. Further, such nonlinearity, and also hysteresis to which the rubber diaphragm is also subjected, may be compensated electrically, as will be described below.

Figure 2:
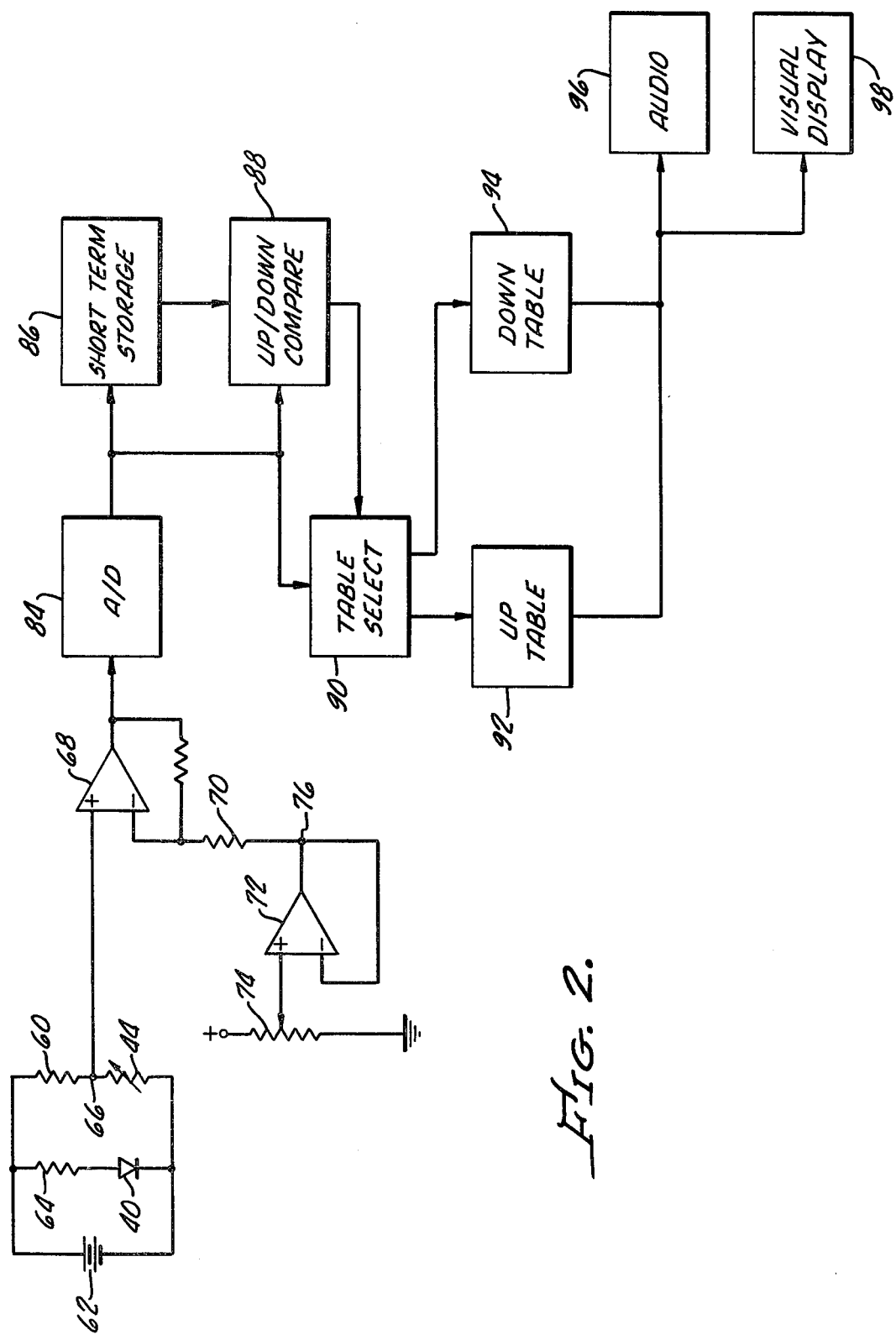
FIG. 2 is a block diagram of an electrical circuit of the apparatus of FIG. 1.

Illustrated in FIG. 2 is a block diagram of an electrical circuit employing the pressure sensor and transducer of FIG. 1. Photosensitive resistor 44, indicated as a variable resistor in FIG. 2, is connected in a voltage divider network with a second resistor 60 in series with a voltage source or battery 62. Light emitting diode 40 is connected in series with a resistor 64, which are both in parallel with the divider circuit 44, 60. The resistance of photocell 44 varies according to the amount of light received by the photocell, and, accordingly, the voltage at point 66, the junction of resistors 44 and 60, will vary with the amount of light received. Voltage at point 66 is fed to the noninverting input of a differential amplifier 68 having its inverting input connected via a resistor 70 to the output of a second differential amplifier 72 that provides a reference to the inverting input of the amplifier 68. THe noninverting input of reference amplifier 72 is provided with a selectively variable voltage from a potentiometer 74. The amplifier output is fed back to its inverting input, whereby its output at point 76 will follow the input voltage selected by potentiometer 74. Potentiometer 74 is set and amplifier 72 and resistor 70 chosen so that the reference signal at the inverting input of amplifier 68 is equal to the voltage at point 66 in the absence of any pressure signal. Therefore amplifier 68 will provide a zero output when the sensed pressure is ambient pressure (atmospheric).

Figure 3:
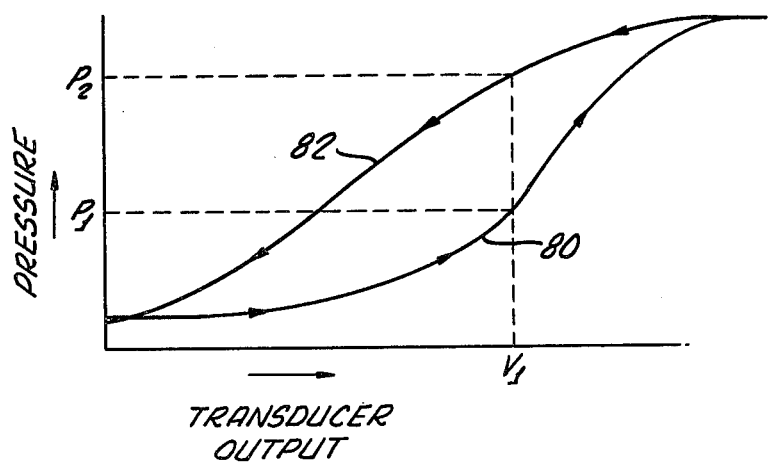
FIG. 3 illustrates a hysteresis curve typical of the flexible diaphragm employed in the transducer.

In a presently preferred embodiment of this invention, correction of errors due to hysteresis and nonlinearity of the flexible diaphragm 50 of pressure tube 56 is most readily handled electronically by appropriate modification of the voltage signal provided at the output of amplifier 68. FIG. 3 illustrates the hysteresis and nonlinearity problems. The voltage output of the transducer follows a first curve 80 when pressure is increasing, and when pressure is decreasing the voltage follows a second nonlinear curve 82, due to the hysteresis of the diaphragm. Accordingly, for a given transducer output voltage level $V_1$, there may be a corresponding pressure of either $P_1$ or $P_2$, as illustrated in FIG. 3. Further, the relation between $V_1$ and each of $P_1$ and $P_2$ is nonlinear.

To effectively compensate for nonlinearity and hysteresis, the voltage signal from amplifier 68 is fed to an analog-to-digital converter 84 which produces a digital code representing the analog voltage value. This code is fed to a short-term storage circuit 86 and also fed directly to an up/down comparison circuit 88 which compares the instantaneous digital signal from the converter 84 with a previous value of this signal to determine which is greater. Comparison circuit 88 effects operation of a table selection circuit 90 which operates much like a switch to steer the digital signal provided from the analog-to-digital converter 84 to either an up table 92 or a down table 94, each of which provides a set of linearized values for the respective hysteresis curves 80 and 82. Each table may be a storage device having pressure values stored at different memory locations. The values stored at the several locations are empirically determined so that a given voltage value from the analog-to-digital converter 84 may be employed to select an address of the particular table at which address is contained the actual linearized value of pressure for the particular digital value used to enter the memory. The up table 92 provides a set of values based upon the increasing pressure curve 80, whereas the down table 94 provides a set of values based upon the decreasing pressure curve 82. The selected table accordingly provides a digital output compensated for both hysteresis and nonlinearity, which is then fed to output equipment, including an audio device 96 and a visual display 98. The audio device 96 may include circuitry to produce an audible frequency according to the magnitude of the input so that, for example, as sensed pressure increases, frequency of the audio output would increase concomitantly. Similarly, the visual display may provide a precise display of the magnitude of the sensed pressure.

The described circuitry for nonlinearity and hysteresis compensation may be mechanized in a number of different ways, but is most readily handled by use of a common microprocessor and suitable programming. The various functions, such as Short Term Storage, Up/Down Compare, Table Select, Up Table, and Down Table, preferably are all performed within the microprocessor and are functions of software. In such an arrangement, the program may be readily changed as changes in manufacturing methods, materials or configuration may require different compensations.

The described apparatus is useful as a clinical instrument for diagnosis and as a biofeedback device for exercising vaginal muscles. As a clinical instrument, a precise quantitative measurement can be provided by a visual digital display to afford an accurate measurement of the strength of muscle contraction. As is well known, the strength of such contractions is an important diagnostic measure. For use as a biofeedback device, the occurrence of vaginal muscle contraction, which may not otherwise be discernible, is readily displayed and identified by either the visual display or an audio tone which varies in frequency as the pressure signal increases.

As the muscles in contact with the outer wall 12 of the tubular member 10 contract, the walls are distorted inwardly to increase the pressure of the confined volume of air and thus to increase the pressure within pressure tube 46. Increase of pressure within the pressure tube causes diaphragm 50 to flex outwardly, thereby progressively blocking more of the light being transmitted through the aperture 38. As less light is transmitted through aperture 38, less light is received by the photo resistor 44, and its resistance increases to provide a pressure signal at point 66. The pressure signal, as previously described, is compared with the reference at the input to amplifier 68, is corrected for nonlinearity and hysteresis, and then employed to provide the described displays.

The described biofeedback and measuring apparatus provides an improved diagnostic and exercising instrument employing an unique, rugged, reliable, yet simple and inexpensive, transducer in a system that affords simple, readily useful visual and audio displays for an inexpensive exercising device and yet has sufficient accuracy for clinical diagnosis.

The foregoing detailed description is to be clearly understood as given by way of illustration and example only, the spirit and scope of this invention being limited solely by the appended claims.

What is claimed is:

1. Apparatus for use in exercising or measuring strength of vaginal muscles comprising
a flexible, hollow tubular member adapted to be compressed in response to vaginal muscle contraction,
transducer means responsive to pressure in said tubular member for generating an electrical signal with a magnitude that varies with pressure, said transducer means comprising
a housing,
a partition dividing said housing into first and second chambers,
a light source in one of said chambers,
a photosensitive resistor in the other of said chambers positioned to receive light transmitted from said source,
an aperture in said partition for transmitting light from said source to said photosensitive resistor,
means in said housing responsive to pressure in said tubular member for controlling the amount of light received by said photosensitive resistor,
said means for controlling the amount of light comprising a pressure tube in said housing having an end adjacent said aperture, said pressure tube being in fluid communication with the interior of said tubular member, and a flexible diaphragm secured to and sealing said end of said pressure tube and adapted to flex so as to progressively block said aperture as pressure in said pressure tube increases,
said diaphragm flexing being subject to hysteresis and having a nonlinear relation to pressure,
means responsive to the resistance of said photosensitive resistor for generating said electrical signal and for modifying said electrical signal to compensate for said hysteresis and nonlinearity,
and indicator means responsive to the compensated electrical signal for providing an indication of intensity of muscle contraction.

2. Apparatus for sensing and indicating vaginal muscle contraction comprising
a flexible, hollow tubular member adapted to experience a change of internal volume in response to compression caused by vaginal muscle contraction,
a light tight housing having a partition separating the interior of the housing into first and second compartments, said partition having an aperture,
a light source in said first compartment,
a light detector in said second compartment positioned to receive light transmitted along a light path through said partition aperture,
a rigid inextensible pressure vessel fixedly mounted within said first compartment, said vessel having an end positioned adjacent said partition aperture,
a flexible diaphragm extending across and sealing said vessel end, said diaphragm being adapted to flex into said light path upon increase of pressure within said vessel, so as to progressively block said aperture as pressure in said vessel increases,
a tube connecting said tubular member to said pressure vessel whereby change of volume of said tubular member changes pressure within said pressure vessel,
said diaphragm flexing toward said aperture and light path nonlinearly with respect to pressure change and being subject to hysteresis as it expands and contracts,
means responsive to said light detector for generating a sensing signal indicative of the amount of light received by the detector,
means for compensating said sensing signal for the nonlinearity and hysteresis of said diaphragm to produce a control signal representing compression of said tubular member,
output means responsive to said control signal for producing an output related to magnitude of said control signal, and
means for transmitting said control signal to said output means.

3. The apparatus of claim 2 wherein said connecting tube comprises a meter length of inextensible tubing whereby volume of air within said tubing experiences minimum change with change in pressure.

4. The apparatus of claim 2 including a visual display responsive to said control signal for providing a visible indication of magnitude of said control signal.

5. The apparatus of claim 2 wherein said means for compensating comprises means for digitizing said sensing signal, direction means for determining the direction of change of said sensing signal, first and second storage table means for storing linearized values of pressure, means responsive to said direction means and to said digitized sensing signal for selecting from one of said tables a compensated value of pressure corrected for nonlinearity and hysteresis of said diaphragm, said output means comprising means for displaying said compensated value.

* * * * *

UNITED STATES PATENT AND TRADEMARK OFFICE
CERTIFICATE OF CORRECTION

PATENT NO. : 4,476,880
DATED : Oct. 16, 1984
INVENTOR(S) : Giem et al.

It is certified that error appears in the above-identified patent and that said Letters Patent is hereby corrected as shown below:

Claim 3 (column 6, line 34), delete the word "meter".

Signed and Sealed this

Sixteenth Day of April 1985

[SEAL]

Attest:

DONALD J. QUIGG

Attesting Officer

Acting Commissioner of Patents and Trademarks